(12) United States Patent
Wang

(10) Patent No.: US 11,586,959 B2
(45) Date of Patent: Feb. 21, 2023

(54) ENVIRONMENTAL STATE ANALYSIS METHOD, AND USER TERMINAL AND NON-TRANSITORY MEDIUM IMPLEMENTING SAME

(71) Applicant: Fulian Precision Electronics (Tianjin) Co., LTD., Tianjin (CN)

(72) Inventor: Shih-Cheng Wang, New Taipei (TW)

(73) Assignee: Fulian Precision Electronics (Tianjin) Co., LTD., Tianjin (CN)

( * ) Notice: Subject to any disclaimer, the term of this patent is extended or adjusted under 35 U.S.C. 154(b) by 526 days.

(21) Appl. No.: 16/835,631

(22) Filed: Mar. 31, 2020

(65) Prior Publication Data

US 2021/0201185 A1  Jul. 1, 2021

(30) Foreign Application Priority Data

Dec. 30, 2019  (CN) .......................... 201911402816.6

(51) Int. Cl.
*G06N 7/00* (2006.01)
*G01N 33/00* (2006.01)
*G06N 20/00* (2019.01)
*G06N 7/06* (2006.01)

(52) U.S. Cl.
CPC .......... *G06N 7/00* (2013.01); *G01N 33/0067* (2013.01); *G06N 20/00* (2019.01)

(58) Field of Classification Search
CPC ....... G06N 7/00; G06N 20/00; G01N 33/0067
See application file for complete search history.

(56) References Cited

U.S. PATENT DOCUMENTS

| 2005/0046584 | A1* | 3/2005 | Breed | B60R 21/01536 340/13.31 |
|---|---|---|---|---|
| 2006/0024654 | A1* | 2/2006 | Goodkovsky | G09B 7/02 434/350 |
| 2006/0208169 | A1* | 9/2006 | Breed | G01S 7/4802 250/221 |
| 2010/0204973 | A1* | 8/2010 | Parkinson | G16B 50/30 703/11 |
| 2014/0180914 | A1* | 6/2014 | Abhyanker | G05D 1/102 705/332 |
| 2016/0175633 | A1* | 6/2016 | Smith | A62C 3/0214 169/61 |
| 2017/0311131 | A1* | 10/2017 | South | G01S 5/14 |
| 2020/0400631 | A1* | 12/2020 | Gao | G01N 27/12 |

FOREIGN PATENT DOCUMENTS

CN  108133295 A  6/2018
CN  110533976 A  12/2019

* cited by examiner

*Primary Examiner* — Nicholas Augustine
(74) *Attorney, Agent, or Firm* — ScienBiziP, P.C.

(57) ABSTRACT

An environmental state analysis method includes obtaining key data that affects an environmental state of a designated place, and determining a degree of influence of the key data on the environmental state of the designated place according to the key data by using an analysis model. The key data includes one or more of environmental protection data, pollution source data, and environmental monitoring data. The environmental state includes one or more of a diffusion speed of harmful gas and a concentration of dust in the air.

15 Claims, 3 Drawing Sheets

ENVIRONMENTAL STATE ANALYSIS METHOD, AND USER TERMINAL AND NON-TRANSITORY MEDIUM IMPLEMENTING SAME

FIELD

The subject matter herein generally relates to environmental monitoring, and more particularly to an environmental state analysis method.

BACKGROUND

Many factors may affect the state of an environment. Analyzing the impact of different factors on the environment is useful and important for many scenarios, such as chemical plants.

BRIEF DESCRIPTION OF THE DRAWINGS

Implementations of the present disclosure will now be described, by way of embodiments, with reference to the attached figures.

DETAILED DESCRIPTION

Figure 1:
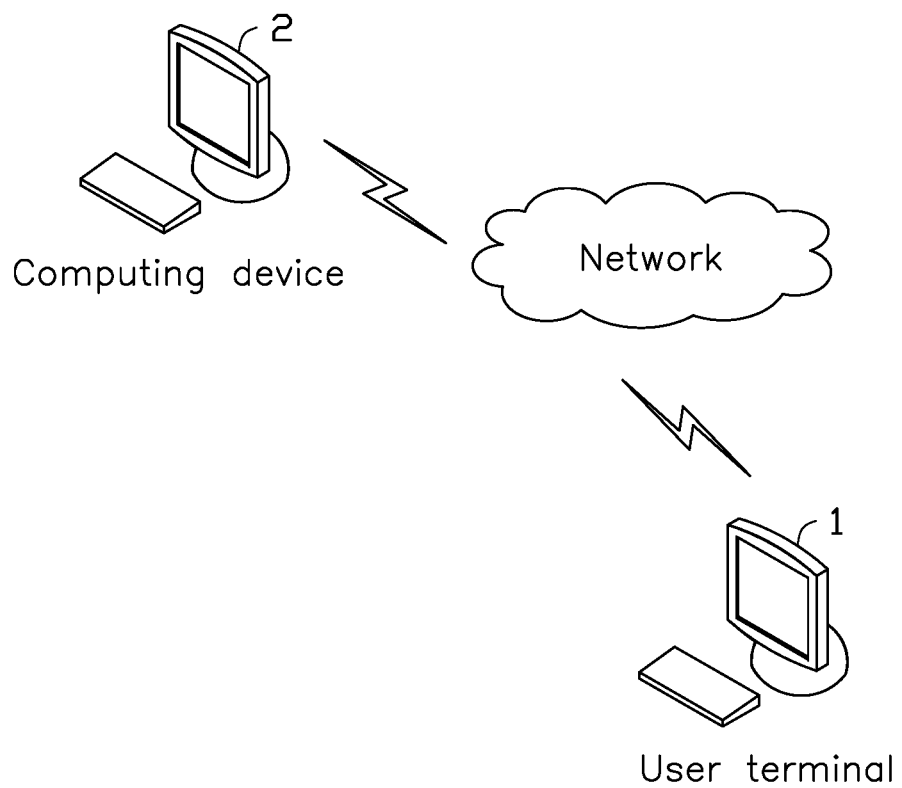
FIG. 1 is a schematic diagram of an embodiment of an application environment of an environmental state analysis method.

It will be appreciated that for simplicity and clarity of illustration, where appropriate, reference numerals have been repeated among the different figures to indicate corresponding or analogous elements. Additionally, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "comprising" means "including, but not necessarily limited to"; it specifically indicates open-ended inclusion or membership in a so-described combination, group, series and the like.

In general, the word "module" as used hereinafter refers to logic embodied in hardware or firmware, or to a collection of software instructions, written in a programming language such as, for example, Java, C, or assembly. One or more software instructions in the modules may be embedded in firmware such as in an erasable-programmable read-only memory (EPROM). It will be appreciated that the modules may comprise connected logic units, such as gates and flip-flops, and may comprise programmable units, such as programmable gate arrays or processors. The modules described herein may be implemented as either software and/or hardware modules and may be stored in any type of computer-readable medium or other computer storage device.

FIG. 1 shows a schematic diagram of an embodiment of an application environment of an environmental state analysis method.

The environmental state analysis method is applied to a user terminal 1. The user terminal 1 establishes a communication connection with a computing device 2 through a network. The network may be a wired network or a wireless network, such as radio, wireless fidelity (WIFI), cellular, satellite, and broadcast.

The user terminal 1 is configured to obtain key data of an environmental state of a designated place, and use the environmental state analysis method to analyze a degree of influence of the key data on an environment of the designated place. The computing device 2 is configured to store different key data, a degree of influence of changes of the key data on the environmental state, and a corresponding relationship between the degree of influence of the key data on the environmental state and a protection strategy.

The user terminal 1 may be an electronic device such as a personal computer, a tablet computer, or the like, on which environmental state analysis software is installed.

The computing device 2 may be an electronic device, such as a personal computer, a server, or the like that can store different key data, the degree of influence of changes in the key data on the environmental state, and the corresponding relationship between the degree of influence of the key data on the environmental state and the protection strategy. The server may be a single server, a server cluster, or a cloud server.

In another embodiment, the different key data, the degree of influence of changes in the key data on the environmental state, and the corresponding relationship between the degree of influence of the key data on the environmental state and the protection strategy may also be stored in the user terminal 1.

Figure 2:
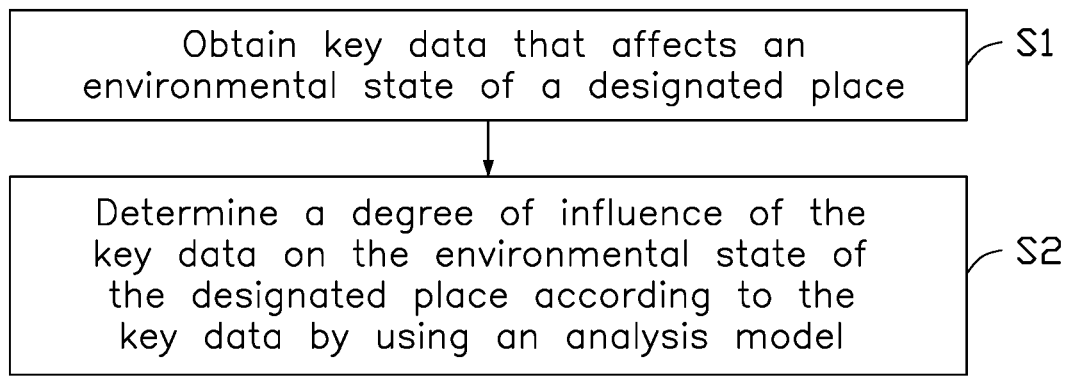
FIG. 2 is a flowchart of the environmental state analysis method.

FIG. 2 shows a flowchart of the environmental state analysis method. According to different requirements, the order of blocks in the flowchart can be changed, and some blocks can be omitted or combined.

Block S1: Key data that affects an environmental state of a designated place is obtained.

The key data includes one or more of environmental protection data, pollution source data, and environmental monitoring data. The environmental protection data includes, but is not limited to, the number of air vents in the designated place, locations of the air vents, the number of fire sprinklers in the designated place, and locations of the fire sprinklers. The pollution source data includes, but is not limited to, the number of ignition sources in the designated place, locations of the ignition sources, the number of fume hoods for discharging toxic and harmful gas in the designated place, and locations of the fume hoods. The environmental monitoring data includes monitoring data related to environmental states such as environmental temperature and environmental humidity.

In one embodiment, the environmental protection data, the pollution source data, and the environmental monitoring data may be received by being input by a user. In another embodiment, the environmental protection data, the pollution source data, and the environmental monitoring data may be obtained by receiving multiple images of the designated place captured by at least one camera device, and identifying the environmental protection data, the pollution source data, and the environmental monitoring data in the images by an image recognition method.

Block S2: A degree of influence of the key data on the environmental state of the designated place is determined according to the key data by using an analysis model, where the environmental state includes one or more of a diffusion speed of harmful gas and a concentration of dust in air.

A method of training the analysis model may include the following:

(1) Acquiring a plurality of data that affects the environmental state of the designated place.

In one embodiment, the plurality of data that affects the environmental state of the designated place includes, but is not limited to, the number of people in the designated place, locations of items in the designated place, orientations of doors, windows, and air vents, changes in ambient temperature and humidity, the number of air purification devices, the number of fire-extinguishing devices, the number of fire sprinklers, and the like.

(2) Analyzing the plurality of data through an environmental state simulation system to determine the key data that affects the environmental state of the designated place and the degree of influence of the key data on the environmental state of the designated place.

A method for determining the key data that affects the environmental state of the designated place and the degree of influence of the key data on the environmental state of the designated place may include the following:

Dividing the plurality of data into a plurality of intervals according to a range of change of each type of data;

Inputting the plurality of data into the environmental state simulation system in sequence according to a change rule of the intervals to determine whether a change in the data will affect the environmental state;

If the change in the data affects the environmental state, determining that the data is the key data that affects the environmental state of the designated place, and correspondingly storing the key data and the degree of influence of the key data on the environmental state in a preset database.

For example, the designated place is an aluminum-magnesium material processing workshop, and the environmental state is a concentration of aluminum and magnesium dust in the air in the designated place. Whether the humidity of the designated place is the key data that affects the environmental state of the designated place is analyzed. All items in the processing workshop and a spatial layout of the items are input into the environmental state simulation system. The environmental state simulation system calculates the concentration of aluminum and magnesium dust for every 1% change in humidity, and whether the concentration of aluminum and magnesium dust changes with the change in humidity is determined. If the concentration of aluminum and magnesium dust changes, the humidity of the designated place is determined to be the key data that affects the environmental state of the designated place. If the concentration of aluminum and magnesium dust does not change, the humidity of the designated place is determined to not be the key data that affects the environmental state of the designated place. The key data and the degree of influence of the key data on the environmental state of the designated place are stored in the preset database.

(3) Importing the key data that affects the environmental state of the designated place and the degree of influence of the key data on the environmental state of the designated place into the analysis model to train parameters of the analysis model.

The method of training the analysis model further includes the following:

Obtaining the key data that affects the environmental state of the designated place and the degree of influence of the key data on the environmental state from the preset database;

Dividing the key data and the degree of influence of the key data into a training set and a verification set;

Establishing an analysis model based on a neural network, and using the training set to train the parameters of the analysis model, where the key data is used as input data of the analysis model, and the degree of influence is used as output data of the analysis model;

Verifying the trained analysis model by using the verification set, and statistically obtaining a prediction accuracy of the trained analysis model according to a verification result;

Determining whether the prediction accuracy is less than a preset threshold;

If the prediction accuracy is not less than the preset threshold, ending the training of the analysis model.

If the prediction accuracy is less than the preset threshold, adjusting a structure of the analysis model and retraining the adjusted analysis model using the training set, where the structure of the analysis model includes at least one of the number of convolution kernels, the number of elements in a pooling layer, and the number of elements in a fully connected layer.

Using the verification set to verify the retrained analysis model, re-statistically obtaining the prediction accuracy of the retrained analysis model based on the verification result, and determining whether the prediction accuracy of the retrained analysis model is less than the preset threshold.

If the re-statistically obtained prediction accuracy is not less than the preset threshold, ending the training of the analysis model.

If the re-statistically obtained prediction accuracy is less than the preset threshold, repeating the steps of adjusting and retraining until the prediction accuracy verified by the verification set is not less than the preset threshold.

The steps in the above training method of the analysis model can be changed according to actual needs, and some steps can be omitted. The training method can be completed online or offline.

In one embodiment, before the key data that affects the environmental state is input into the analysis model, the method further includes the following:

Processing the key data that affects the environmental state numerically by mapping the key data between 0 and 1 according to a preset ratio by the analysis model.

For example, the number of personnel that can be analyzed by the analysis model is 2,000, and the number of personnel in the designated place is 500, so a ratio of 0.25 is input as the key data into the analysis model. In another example, the number of air vents that can be analyzed by the analysis model is 1,000, and the number of air vents in the designated place is 100, so a ratio of 0.1 is input as the key data into the analysis model. Thus, a plurality of the key data related to a fire-control status is numerically processed.

The numerically processed key data is input into the analysis model, and the degree of influence of the key data on the environmental state is output. The analysis model numerically processes the degree of influence by mapping the degree of influence between 0 and 1 according to the preset ratio. For example, a concentration of dust in air that can be analyzed by the analysis model is 20 mg/m3. The key data that affects the concentration of dust is input into the analysis model and analyzed, and the degree of influence of the key data on the concentration of dust output by the analysis model is 0.02. The degree of influence is multiplied by the concentration of dust that can be analyzed by the analysis model, so the degree of influence after being numerically processed is 0.4 mg/m3.

In another embodiment, block S2 further includes the following:

The corresponding protection strategy is found in the preset database and implemented according to the degree of influence on the environmental state of the designated place, where the preset database stores a correspondence between the degree of influence and the protection strategy. For example, the analysis model analyzes the effect of temperature on a dust concentration in air. For every 2° C. increase in temperature, the dust concentration in the air increases by 0.02 mg/m3. When the temperature reaches 20° C., the dust concentration in the air meets a threshold tolerance for the dust concentration. The protection strategy is to issue a prompt to control an air conditioning system to cool the air.

It should be understood that the embodiments are for illustrative purposes only and are not limited in scope by the aforementioned embodiments.

Figure 3:
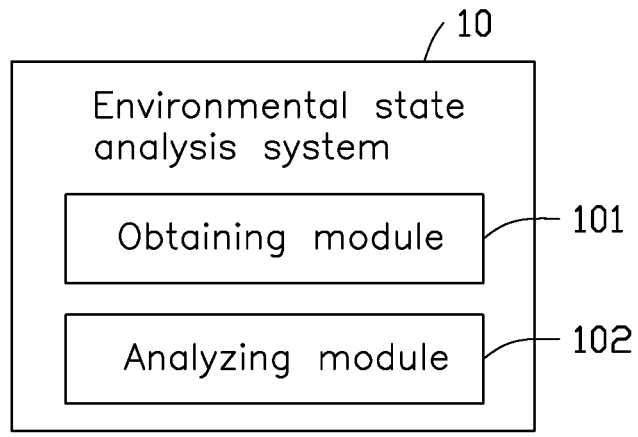
FIG. 3 is a schematic diagram of an embodiment of an environmental state analysis system.

FIG. 3 is a schematic diagram of an embodiment of an environmental state analysis system 10.

In some embodiments, the environmental state analysis system 10 runs in a user terminal. The user terminal is connected to a computing device through a network. The environmental state analysis system 10 may include a plurality of functional modules composed of program code segments. The program code segments in the environmental state analysis system 10 may be stored in a memory of the user terminal and executed by at least one processor to implement an environmental state analysis function.

In one embodiment, the environmental state analysis system 10 may be divided into a plurality of functional modules according to functions performed by the environmental state analysis system 10. Referring to FIG. 3, the functional modules may include an obtaining module 101 and an analyzing module 102.

The obtaining module 101 is configured to obtain key data that affects an environmental state of a designated place. The obtaining module 101 may implement functions of the method in block S1 as described above, and will not be described further.

The analyzing module 102 is configured to determine a degree of influence of the key data on the environmental state of the designated place according to the key data by using an analysis model. The analyzing module 102 may implement functions of the method in block S2 as described above, and will not be described further.

Figure 4:
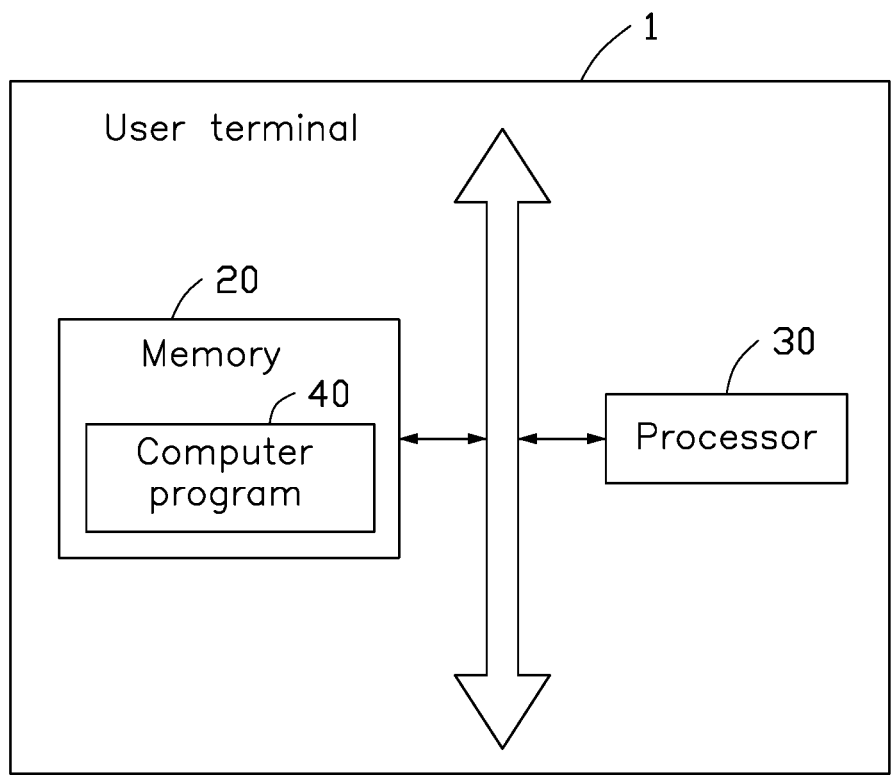
FIG. 4 is a schematic diagram of an embodiment of a user terminal.

FIG. 4 is a schematic diagram of an embodiment of the user terminal 1.

The user terminal 1 includes a memory 20, a processor 30, and a computer program 40, such as an environmental state analysis program, stored in the memory 20 and executable by the processor 30. When the processor 30 executes the computer program 40, the blocks in the embodiment of the environmental state analysis method shown in FIG. 2 may be implemented. Alternatively, when the processor 30 executes the computer program 40, the functions of the modules in the embodiment of the environmental state analysis system 10 shown in FIG. 3 may be implemented.

The user terminal 1 may be a computing device such as a desktop computer, a notebook, a palmtop computer, and a cloud server. Those skilled in the art should understand that the schematic diagram of the user terminal 1 does not constitute a limitation of the user terminal 1. The user terminal 1 may include more or fewer components than shown, or may combine some components. For example, the user terminal 1 may further include an input-output device, a network access device, a bus, and the like.

The processor 30 may be a central processing unit (CPU), or may be other general-purpose processors, digital signal processors (DSPs), application specific integrated circuits (ASICs), a Field-Programmable Gate Array (FPGA) or other programmable logic devices, discrete gate or transistor logic devices, discrete hardware components, etc. The general-purpose processor may be a microprocessor, or the processor 30 may be any conventional processor, etc. The processor 30 is a control center of the user terminal 1 and uses various interfaces and lines to connect various parts of the user terminal 1.

The memory 20 may be configured to store the computer program 40, and the processor 30 may execute the computer program 40. The data in the memory 20 may realize various functions of the user terminal 1. The memory 20 may mainly include a storage program area and a storage data area, wherein the storage program area may store an operating system, at least one application required by a function (such as a sound playback function, an image playback function, etc.). The storage data area may store data (such as audio data) and the like created according to the use of the user terminal 1. In addition, the memory 20 may include a high-speed random access memory, and may also include a non-volatile memory, such as a hard disk, an internal memory, a plug-in hard disk, a smart media card (SMC), a secure digital (SD) card, flash card, at least one disk storage device, flash memory device, or other non-volatile solid-state storage device.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. An environmental state analysis method comprising:
obtaining key data that affects an environmental state of a designated place, wherein the key data comprises one or more of environmental protection data, pollution source data, and environmental monitoring data;
training an analysis model, comprising:
acquiring a plurality of data that affects the environmental state of the designated place;
analyzing the plurality of data through an environmental state simulation system to determine the key data that affects the environmental state of the designated place and a degree of influence of the key data on the environmental state of the designated place, wherein, the designated place is an aluminum-magnesium material processing workshop, and the environmental state is a concentration of aluminum and magnesium dust, items in the aluminum-magnesium processing workshop and a spatial layout of the items are input into the environmental state simulation system, and the environmental state simulation system calculates the concentration of aluminum and magnesium dust for change of humidity, if the concentration of aluminum and magnesium dust changes with the change of the humidity, the humidity of the designated place is determined to be the key data;
importing the key data that affects the environmental state of the designated place and the degree of influence of the key data on the environmental state of the designated place into the analysis model to train parameters of the analysis model; and
determining the degree of influence of the key data on the environmental state of the designated place according to the key data by using the analysis model, wherein the environmental state comprises one or more of a diffusion speed of harmful gas and a concentration of dust in air.

2. The environmental state analysis method of claim 1, wherein a method for determining the key data that affects the environmental state of the designated place and the degree of influence of the key data on the environmental state of the designated place comprises:
dividing the plurality of data into a plurality of intervals according to a range of change of each type of data;
inputting the plurality of data into the environmental state simulation system in sequence according to a change rule of the intervals to determine whether a change in the data will affect the environmental state; and
if the change in the data affects the environmental state, determining that the data is the key data that affects the environmental state of the designated place, and correspondingly storing the key data and the degree of influence of the key data on the environmental state in a preset database.

3. The environmental state analysis method of claim 2, wherein the method of training the analysis model further comprises:
obtaining the key data that affects the environmental state of the designated place and the degree of influence of the key data on the environmental state from the preset database;
dividing the key data and the degree of influence of the key data into a training set and a verification set;
establishing an analysis model based on a neural network, and using the training set to train the parameters of the analysis model, wherein the key data is used as input data of the analysis model, and the degree of influence is used as output data of the analysis model;
verifying the trained analysis model by using the verification set, and statistically obtaining a prediction accuracy of the trained analysis model according to a verification result;
determining whether the prediction accuracy is less than a preset threshold; and
if the prediction accuracy is not less than the preset threshold, ending the training of the analysis model.

4. The environmental state analysis method of claim 3, wherein the method of training the analysis model further comprises:
if the prediction accuracy is less than the preset threshold, adjusting a structure of the analysis model and retraining the adjusted analysis model using the training set, wherein the structure of the analysis model comprises at least one of the number of convolution kernels, the number of elements in a pooling layer, and the number of elements in a fully connected layer;
using the verification set to verify the retrained analysis model, re-statistically obtaining the prediction accuracy of the retrained analysis model based on the verification result, and determining whether the prediction accuracy of the retrained analysis model is less than the preset threshold;
if the re-statistically obtained prediction accuracy is not less than the preset threshold, ending the training of the analysis model; and
if the re-statistically obtained prediction accuracy is less than the preset threshold, repeating the steps of adjusting and retraining the analysis model until the prediction accuracy verified by the verification set is not less than the preset threshold.

5. The environmental state analysis method of claim 1, further comprising:
finding a corresponding protection strategy in the preset database according to the degree of influence on the environmental state of the designated place and implementing the corresponding protection strategy, wherein the preset database stores a correspondence between the degree of influence and the protection strategy, the corresponding protection strategy is to issue a prompt to control an air conditioning system to cool the air.

6. A user terminal comprising:
a processor; and
a memory storing a plurality of instructions, which when executed by the processor, cause the processor to:
obtain key data that affects an environmental state of a designated place, wherein the key data comprises one or more of environmental protection data, pollution source data, and environmental monitoring data;
train an analysis model, wherein "training the analysis model" comprises:
acquiring a plurality of data that affects the environmental state of the designated place;
analyzing the plurality of data through an environmental state simulation system to determine the key data that affects the environmental state of the designated place and a degree of influence of the key data on the environmental state of the designated place, wherein,
the designated place is an aluminum-magnesium material processing workshop, and the environmental state is a concentration of aluminum and magnesium dust, items in the aluminum-magnesium processing workshop and a spatial layout of the items are input into the environmental state simulation system, and the environmental state simulation system calculates the concentration of aluminum and magnesium dust for change of humidity, if the concentration of aluminum and magnesium dust changes with the change of the humidity, the humidity of the designated place is determined to be the key data;
importing the key data that affects the environmental state of the designated place and the degree of influence of the key data on the environmental state of the designated place into the analysis model to train parameters of the analysis model; and
determine the degree of influence of the key data on the environmental state of the designated place according to the key data by using the analysis model, wherein the environmental state comprises one or more of a diffusion speed of harmful gas and a concentration of dust in air.

7. The user terminal of claim 6, wherein the processor determines the key data that affects the environmental state of the designated place and the degree of influence of the key data on the environmental state of the designated place by:

dividing the plurality of data into a plurality of intervals according to a range of change of each type of data;

inputting the plurality of data into the environmental state simulation system in sequence according to a change rule of the intervals to determine whether a change in the data will affect the environmental state; and if the change in the data affects the environmental state, determining that the data is the key data that affects the environmental state of the designated place, and correspondingly storing the key data and the degree of influence of the key data on the environmental state in a preset database.

8. The user terminal of claim 7, wherein the processor further trains the analysis model by:

obtaining the key data that affects the environmental state of the designated place and the degree of influence of the key data on the environmental state from the preset database;

dividing the key data and the degree of influence of the key data into a training set and a verification set;

establishing an analysis model based on a neural network, and using the training set to train the parameters of the analysis model, wherein the key data is used as input data of the analysis model, and the degree of influence is used as output data of the analysis model;

verifying the trained analysis model by using the verification set, and statistically obtaining a prediction accuracy of the trained analysis model according to a verification result;

determining whether the prediction accuracy is less than a preset threshold; and if the prediction accuracy is not less than the preset threshold, ending the training of the analysis model.

9. The user terminal of claim 8, wherein the processor further trains the analysis model by:

if the prediction accuracy is less than the preset threshold, adjusting a structure of the analysis model and retraining the adjusted analysis model using the training set, wherein the structure of the analysis model comprises at least one of the number of convolution kernels, the number of elements in a pooling layer, and the number of elements in a fully connected layer;

using the verification set to verify the retrained analysis model, re-statistically obtaining the prediction accuracy of the retrained analysis model based on the verification result, and determining whether the prediction accuracy of the retrained analysis model is less than the preset threshold;

if the re-statistically obtained prediction accuracy is not less than the preset threshold, ending the training of the analysis model; and if the re-statistically obtained prediction accuracy is less than the preset threshold, repeating the steps of adjusting and retraining the analysis model until the prediction accuracy verified by the verification set is not less than the preset threshold.

10. The user terminal of claim 6, wherein the processor is further configured to:

find a corresponding protection strategy in the preset database according to the degree of influence on the environmental state of the designated place and implement the corresponding protection strategy, wherein the preset database stores a correspondence between the degree of influence and the protection strategy, the corresponding protection strategy is to issue a prompt to control an air conditioning system to cool the air.

11. A non-transitory storage medium having stored thereon instructions that, when executed by a processor of a user terminal, causes the processor to perform an environmental state analysis method, wherein the method comprises:

obtaining key data that affects an environmental state of a designated place, wherein the key data comprises one or more of environmental protection data, pollution source data, and environmental monitoring data; and training an analysis model, comprising:

acquiring a plurality of data that affects the environmental state of the designated place;

analyzing the plurality of data through an environmental state simulation system to determine the key data that affects the environmental state of the designated place and a degree of influence of the key data on the environmental state of the designated place, wherein, the designated place is an aluminum-magnesium material processing workshop, and the environmental state is a concentration of aluminum and magnesium dust, items in the aluminum-magnesium processing workshop and a spatial layout of the items are input into the environmental state simulation system, and the environmental state simulation system calculates the concentration of aluminum and magnesium dust for change of humidity, if the concentration of aluminum and magnesium dust changes with the change of the humidity, the humidity of the designated place is determined to be the key data;

importing the key data that affects the environmental state of the designated place and the degree of influence of the key data on the environmental state of the designated place into the analysis model to train parameters of the analysis model; and determining the degree of influence of the key data on the environmental state of the designated place according to the key data by using the analysis model, wherein the environmental state comprises one or more of a diffusion speed of harmful gas and a concentration of dust in air.

12. The non-transitory storage medium of claim 11, wherein a method for determining the key data that affects the environmental state of the designated place and the degree of influence of the key data on the environmental state of the designated place comprises:

dividing the plurality of data into a plurality of intervals according to a range of change of each type of data;

inputting the plurality of data into the environmental state simulation system in sequence according to a change rule of the intervals to determine whether a change in the data will affect the environmental state; and if the change in the data affects the environmental state, determining that the data is the key data that affects the environmental state of the designated place, and correspondingly storing the key data and the degree of influence of the key data on the environmental state in a preset database.

13. The non-transitory storage medium of claim 12, wherein the method of training the analysis model further comprises:

obtaining the key data that affects the environmental state of the designated place and the degree of influence of the key data on the environmental state from the preset database;

dividing the key data and the degree of influence of the key data into a training set and a verification set;

establishing an analysis model based on a neural network, and using the training set to train the parameters of the analysis model, wherein the key data is used as input data of the analysis model, and the degree of influence is used as output data of the analysis model;

verifying the trained analysis model by using the verification set, and statistically obtaining a prediction accuracy of the trained analysis model according to a verification result;

determining whether the prediction accuracy is less than a preset threshold; and if the prediction accuracy is not less than the preset threshold, ending the training of the analysis model.

14. The non-transitory storage medium of claim 13, wherein the method of training the analysis model further comprises:

if the prediction accuracy is less than the preset threshold, adjusting a structure of the analysis model and retraining the adjusted analysis model using the training set, wherein the structure of the analysis model comprises at least one of the number of convolution kernels, the number of elements in a pooling layer, and the number of elements in a fully connected layer;

using the verification set to verify the retrained analysis model, re-statistically obtaining the prediction accuracy of the retrained analysis model based on the verification result, and determining whether the prediction accuracy of the retrained analysis model is less than the preset threshold;

if the re-statistically obtained prediction accuracy is not less than the preset threshold, ending the training of the analysis model; and if the re-statistically obtained prediction accuracy is less than the preset threshold, repeating the steps of adjusting and retraining the analysis model until the prediction accuracy verified by the verification set is not less than the preset threshold.

15. The non-transitory storage medium of claim 11, wherein the method further comprises:

finding a corresponding protection strategy in the preset database according to the degree of influence on the environmental state of the designated place and implementing the corresponding protection strategy, wherein the preset database stores a correspondence between the degree of influence and the protection strategy, the corresponding protection strategy is to issue a prompt to control an air conditioning system to cool the air.

* * * * *